United States Patent
Clarence-Smith et al.

(10) Patent No.: US 9,896,416 B2
(45) Date of Patent: *Feb. 20, 2018

(54) PIPERIDINIUM QUATERNARY SALTS

(71) Applicant: Chase Pharmaceuticals Corporation, Washington, DC (US)

(72) Inventors: Kathleen E. Clarence-Smith, Washington, DC (US); Thomas N. Chase, Washington, DC (US)

(73) Assignee: Chase Parmaceuticals Corporation, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/419,381

(22) PCT Filed: Jul. 30, 2013

(86) PCT No.: PCT/US2013/052626
§ 371 (c)(1),
(2) Date: Feb. 3, 2015

(87) PCT Pub. No.: WO2014/025569
PCT Pub. Date: Feb. 13, 2014

(65) Prior Publication Data
US 2015/0203452 A1    Jul. 23, 2015

Related U.S. Application Data

(60) Provisional application No. 61/681,415, filed on Aug. 9, 2012.

(51) Int. Cl.
*C07D 211/46* (2006.01)
*A61K 31/45* (2006.01)

(52) U.S. Cl.
CPC ................. *C07D 211/46* (2013.01)

(58) Field of Classification Search
CPC .................. C07D 211/40; C07D 211/54
USPC ................................ 546/216, 218
See application file for complete search history.

(56) References Cited

U.S. PATENT DOCUMENTS 9,561,218 B2 * 2/2017 Clarence-Smith . A61K 31/4709
2004/0242887 A1 12/2004 Alken et al.

FOREIGN PATENT DOCUMENTS

| CN | 101490003 | | 7/2009 |
|---|---|---|---|
| DE | 106643 | * | 6/1974 |
| WO | 2007123456 | | 11/2007 |
| WO | 2007123465 | | 11/2007 |
| WO | 2011/114195 A1 | | 9/2011 |
| WO | WO2011114195 | * | 9/2011 |

OTHER PUBLICATIONS

Christian et al. "Diphenyl-alkoxy . . . " CA82:155841 (1975).*
Watcher "Water membrane partitioning . . . " dessertation p. 51-69 (2008).*
Scapecchi et al. "Dialkylaminoalkyl . . . " Bioorg. Med. Chem. 2(10) 106101074 (1994).*
Yoshimura et al. "Neurophysiology . . . " Rev. in urology 5(suppl 8) p. S3-S10 (2003).*
Barash et al. "Clinical anesthesia . . . " p. 346-347 (2009).*
Pak et al. "Trospium . . . " Current Urol. Reports v. 4, 436-440 (2003).*
Scapecchi et al. "Dialkylamino . . . " CA122:204554 (1995).*
Scapecchi et al, Bioorganic Medicinal Chemistry, vol. 2, No. 10, pp. 1061-1074, 1994.*
Propiverine—Compound Summary (CID 41125), PubChem Compound, Aug. 8, 2005, 3 pages.
William P. Jencks, et al. "Decreasing Reactivity with Increasing Nucleophile Basicity. The Effect of Solvation on $\beta_{nuc}$ for Phosphoryl Transfer to Amines" J. Am. Chem. Soc. 1986; pp. 479-483, vol. 108.
International Search Report for PCT/US2013/052626 dated Nov. 26, 2013 [PCT/ISA/210].
Written Opinion for PCT/US2013/052626 dated Nov. 26, 2013 [PCT/ISA/237].
Andersson, "Antimuscarinics for treatment of overactive bladder", The Lancet Neurology, 3:46-53 (2004).
Communication for European Patent Application 13827594.6 dated Jan. 12, 2016, with Supplementary European Search Report (dated Dec. 18, 2015).
Klosa, "Synthese von Derivaten des Benzilsaureesters mit N-Methyl-hydroxy-piperidin", Journal fur praktische Chemie, 4(16):71-82 (1962), EP Communication dated Jan. 12, 2016.
Beltrame et al., "Kinetics of the reaction between piperdine and halonitronaphthalenes", Gazzetta Chimica Italiana, 92:351-364 (1962), Abstract No. XP-002752389, EP Communication dated Jan. 12, 2016.
You, "Pharmaceutical Chemistry", China Medical Science Press, pp. 131-133 (Dec. 2011).
Office Action Search for Chinese Application No. 2013800420853, dated Aug. 29, 2016.
Office Action for Chinese Application No. 2013800420853 dated Oct. 8, 2016.

* cited by examiner

*Primary Examiner* — Zinna Northington-Davis
(74) *Attorney, Agent, or Firm* — Sughrue Mion, PLLC

(57) ABSTRACT

There are described new 1-alkyl-1-methyl-4-[(2,2-diphenyl-2-propoxy)acetoxy]piperidinium halides and pharmaceutical compositions comprising a 1-alkyl-1-methyl-4-[(2,2-diphenyl-2-propoxy)acetoxy]piperidinium halide as an active ingredient. These products are non-selective muscarinic acetylcholine receptor antagonists acting in the periphery and not in the brain.

9 Claims, No Drawings

PIPERIDINIUM QUATERNARY SALTS

FIELD OF THE INVENTION

The present invention relates to new 1-alkyl-1-methyl-4-[(2,2-diphenyl-2-propoxy)acetoxy]piperidinium halides and to pharmaceutical compositions comprising a 1-alkyl-1-methyl-4-[(2,2-diphenyl-2-propoxy)acetoxy]piperidinium halide as an active ingredient. More particularly, it relates to alkylpropiverinium halides, which are non-selective antagonists of the muscarinic acetylcholine receptor (mAChR), acting in the periphery and not in the brain.

BACKGROUND OF THE INVENTION—PRIOR ART

The 1-methyl-4-[(2,2-diphenyl-2-propoxy)acetoxy]piperidine hydrochloride (propiverine hydrochloride) is a non-selective peripheral anticholinergic agent having an affinity for the mAChR subtypes M1-M5. It is currently used to treat people who have urinary problems caused by an overactive bladder or by spinal cord injuries. It works by preventing spasms of the bladder muscle, thus being of help to reduce the episodes of urinary incontinence or reduce the feeling of urgency that bladder spasms can cause.

Propiverine hydrochloride is available in 15-mg tablets for immediate release to be administered twice per day or in 30-mg modified-release capsules to be administered once per day, such that the propiverine hydrochloride active ingredient is administered at the recommended daily dose of 30 mg in the above indications. However, an anticholinergic agent, such as propiverine, could be used for the treatment of a series of other disorders.

In chronic obstructive pulmonary disease (COPD) and asthma, cholinergic mechanisms contribute to increased bronchoconstriction and mucus secretion that limit airflow (Buels K S, Fryer A D. Handb Exp Pharmacol. 2012; 208, 317-41).

In cancers derived from epithelial and in endothelial cancer, the ability of muscarinic agonists to stimulate growth has been shown for melanoma, pancreatic, breast, ovarian, prostate and brain cancers, suggesting that M3 antagonists will also inhibit growth of these tumors (Spindel E R. Handb Exp Pharmacol. 2012; 208, 451-468).

The stratified epithelium enveloping the skin and lining the surfaces of oral and vaginal mucosa is comprised by keratinocytes that synthesize, secrete, degrade, and respond to ACh via muscarinic and nicotinic receptors express a unique combination of mAChR subtypes at each stage of their development. Drugs that block mAChRs, such as propiverine hydrochloride, have the potential of treating patients suffering from non-healing wounds, mucocutaneous cancers, and various autoimmune and inflammatory diseases. Successful therapy of pemphigus lesions with topical pilocarpine and disappearance of psoriatic lesions due to systemic atropine therapy illustrate that such a therapeutic approach is useful (Grando S. A. Handb Exp Pharmacol. 2012; 208, 429-450).

An anticholinergic agent having the properties of propiverine hydrochloride could also be useful in treating sialorrhea (Arbouw M. E. et al. Neurology. 2010 Apr. 13; 74/15, 1203-1207) and Ménière's disease.

Moreover, an anticholinergic agent having the properties of propiverine hydrochloride should antagonize the peripheral dose-limiting side effects of acetylcholine-esterase inhibitors (AChEIs), and thus enable the use of higher and therefore more effective doses of AChEIs in the treatment of Alzheimer-type dementia, post-surgical delirium, Mild Cognitive Impairment (MCI), and related central nervous system (CNS) hypocholinergic syndromes.

SUMMARY OF THE INVENTION

The present invention derives from the observation that CNS adverse events are of particular concern with mAChR antagonists as muscarinic receptors are prominent in the CNS and play an important role in memory, vigilance, problem solving, stimulus, and response processing. However, surprisingly, cognitive impairment traditionally has not been evaluated in clinical trials with muscarinic receptor antagonists (reviewed in Kessler et al, 2011; Plos One, Vol. 6, Issue 2, e26728, February 2011—www.plosone.org). Yet, Perry et al. (2003) found an increased occurrence of Alzheimer's disease (AD) related to a prolonged exposure to mAChR antagonists in patients with Parkinson's disease raising the concern that chronic antimuscarinic treatment may increase the risk of AD or accelerate AD pathogenesis. Antagonism of cholinergic function in the brain has also been shown to lead to decreased cognitive function, and can precipitate dementia (Paquette et al, 2011). Furthermore, in a mouse tauopathy model of Alzheimer's disease pathology, antagonism of muscarinic receptors in the brain was found to boost the neurodegenerative process and to increase inflammation (Yoshiyama et al, 2012).

Even though propiverine hydrochloride is an essentially peripherally-acting anticholinergic agent, some concerns could arise in case of need of administering high doses thereof.

Thus, the present invention provides new quaternary salts of propiverine which are much less lipophilic than propiverine hydrochloride and, by consequence, do not cross the BBB.

Surprisingly, it has been found that quaternarization of propiverine does not involve a loss of the affinity for the muscarinic receptors; on the contrary, the new 1-alkyl-1-methyl-4-[(2,2-diphenyl-2-propoxy)acetoxy]piperidinium halides (alkylpropiverinium halides) show at least the same affinity for all the mAChR subtypes M1-M5 as that of propiverine hydrochloride.

DETAILED DESCRIPTION

The present invention provides novel 1-alkyl-1-methyl-4-[(2,2-diphenyl-2-propoxy)acetoxy]piperidinium halides having the formula I

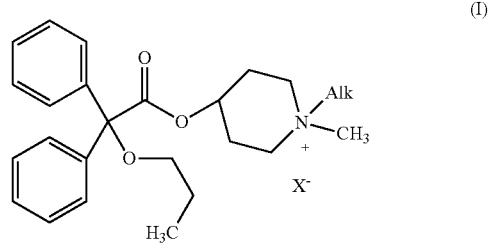

wherein X is a halogen selected from the group consisting of chlorine, bromine and iodine and Alk is a $(C_1-C_4)$alkyl group.

Advantageously, Alk is ethyl, propyl, isopropyl, n-butyl or, preferably methyl.

These quaternary salts, are specially indicated for the treatment of Overactive Bladder Syndrome (OABS), chronic obstructive pulmonary disease (COPD), and asthma, but are also useful for example in the treatment of the aforementioned diseases. They are at least as active as anticholinergic agents as propiverine, hydrochloride, but have a strictly peripheral action.

The 1-alkyl-1-methyl-4-[(2,2-diphenyl-2-propoxy)acetoxy]piperidinium halides of the present invention are prepared by reacting the 1-methyl-4-[(2,2-diphenyl-2-propoxy)acetoxy]piperidine (propiverine base) with a compound of formula Alk-X, wherein Alk and X are as defined above.

The propiverine base starting material can be obtained as crude product as described in WO 2011/114195 or by hydrolysis of propiverine hydrochloride which is an easily available commercial product, also obtainable for example as described in DD 106643, CN 1285348, CN 102218063 (A) KR 2005-0011138, KR 2005-0011139, KR20110111782 (A) or in the aforesaid WO 2011/114195.

According to the present invention, a typical process uses propiverine hydrochloride as starting material and comprises (a) treating an aqueous suspension of propiverine hydrochloride with an inorganic base and recovering the crude propiverine base by extraction from an organic solvent and evaporation of the solvent; and (b) treating the residue with a ($C_1$-$C_4$)alkyl halide in an alcoholic solution and isolating the 1-alkyl-1-methyl-4-[(2,2-diphenyl-2-propoxy)acetoxy]piperidinium halide which precipitates.

Step (a) is a simple hydrolysis which is carried out by suspending propiverine hydrochloride in water and adding an alkaline hydroxide, carbonate or bicarbonate, in particular sodium or potassium hydroxide or carbonate. The reaction is instantaneous. The propiverine base which is present in the mixture is recovered by extraction from an organic solvent, which may be a hydrocarbon, such as toluene or cyclohexane; an ester, such as ethyl acetate; or an ether, such as dioxane or tetrahydrofuran; and by evaporation of the solvent.

In step (b), the residue, consisting of crude propiverine base, is dissolved in an alcoholic solvent, such as methanol or ethanol. The solution is added with the calculated amount of an alkyl halide of formula Alk-X and let to react until the precipitation of is complete, thus allowing the isolation of 1-alkyl-1-methyl-4-[(2,2-diphenyl-2-propoxy)acetoxy]piperidinium halide by filtration. The alkyl halide reacting agent is a ($C_1$-$C_4$)alkyl halide such as a methyl, ethyl, propyl, isopropyl, isobutyl halide, preferably methyl chloride, methyl bromide or methyl iodide. The reaction is carried out at a temperature of from 15 to 40° C., preferably at 15-30° C. when the alkyl halide is methyl chloride, methyl bromide or methyl iodide. Normally, the quaternary salt formation reaction is complete after 10-24 hours and the pure final product is isolated by filtration and washing with an alcohol.

According to the present invention, the starting propiverine base crude product may also be the crude product described in DD 106643, CN 1285348, KR 2005-0011138, KR 2005-0011139 or WO 2011/114195.

In this case, step (a) above is replaced by a step (a1) wherein crude propiverine base is prepared either by reacting an ester, preferably the methyl, ethyl or propyl ester, of 2,2-diphenyl-2-propoxyacetic acid with 1-methylpiperidin-4-ol, directly (KR 2005-001139, WO 2011/114195) or via previous hydrolysis of the ester to the corresponding 2,2-diphenyl-2-propoxyacetic acid (KR 2005-001138); or by reacting 1-methyl-4-(2,2-diphenyl-2-chloro)acetoxypiperidine with n-propanol (DD 106643, CN 1285348); and step (b) is the above-illustrated one.

In order to evaluate the inability of the compounds of formula I of crossing the BBB, their log P has been determined. Log P values are known as a measure of the lipophilicity of a drug and are predictive of how well a drug will cross the Blood Brain Barrier (BBB). In order to confirm that 1-alkyl-1-methyl-4-[(2,2-diphenyl-2-propoxy)acetoxy]piperidinium halides of the invention are excluded from the brain, Log P values were calculated for propiverine hydrochloride in comparison with a representative compound of formula I (Alk=$CH_3$), X=I, namely the 1,1-dimethyl-4-[(2,2-diphenyl-2-propoxy)acetoxy]piperidinium iodide (methylpropiverinium iodide), using LigandScout software. As the result, the log P value of methylpropiverinium iodide is more than 10-fold lower than that of propiverine hydrochloride, demonstrating that penetration of the BBB by the product of the invention will be minimal, much less that that observed with propiverine hydrochloride which is an anticholinergic agent acting mostly peripherally.

In order to determine the affinity of the alkylpropiverinium halides of the invention for the muscarinic receptor, the in vitro binding of a representative compound, methylpropiverinium iodide ("Compound"), to the mAChR subtypes was measured using homogeneous time-resolved fluorescence (HTRF), a method that combines time-resolved fluorescence (TRF) and fluorescence energy transfer (FRET) techniques. The assay involved cells transiently expressing the muscarinic M1, M2, M3, M4, and M5 receptors labeled with terbium cryptate. The affinities of the Compound for the receptors M1-M5, in comparison with propiverine hydrochloride were determined in 8-point concentration-response curves, serially diluted 1:10 starting at 10 μM and performed in duplicate. The final Compound concentrations tested were 10 μM, 100 nM, 10 nM, 1 nM, 0.1 nM, and 0.01 nM. Cells were incubated for 1 hour in the presence of 5 μL of labeled ligand (telenzepine derivative) at final concentration approximating Kd. Readout was conducted on a PHERAstar flash lamo.

In this test, the Compound, exhibited a similar potency as propiverine hydrochloride on all muscarinic subtypes (M1 to M5).

The above tests show that the 1-alkyl-1-methyl-4-[(2,2-diphenyl-2-propoxy)acetoxy]piperidinium halides of the present invention are at least as affine as propiverine hydrochloride for all the mAChR subtypes M1-M5, and that, thanks to their inability to cross the BBB, they may be used, even at high doses, for treating all the aforementioned diseases without inducing anticholinergic adverse effects in the CNS.

Therefore, said compounds of formula I can be used as active ingredients in pharmaceutical compositions, in admixture with a pharmaceutical carrier.

Thus, the present invention further provides a pharmaceutical composition comprising, as an active ingredient, an effective amount of an 1-alkyl-1-methyl-4-[(2,2-diphenyl-2-propoxy)acetoxy]piperidinium halide of formula (I) above, in admixture with a pharmaceutical carrier.

In the compositions of the present invention the alkylpropiverinium halide of formula (I) is present in an amount of from 5 mg to 250 mg, advantageously from 15 mg to 250 mg, preferably from 31 to 250 mg, in admixture with said pharmaceutical carrier.

This composition is normally formulated in a dosage unit form, in particular in slow release capsules, immediate release capsules, slow release tablets, fast-dissolving tablets, orodispersible tablets, sublingual tablets, oral solution, intravenous solution, aerosols, eye drops, suppositories, skin patch, skin cream, skin unguent, skin gel.

In said unit form the active ingredient may be mixed with a pharmaceutical carrier according to known technologies, for example in tablets or capsules in IR or in ER form or also a multilayer tablet wherein the active ingredient is formulated, in one layer, in an IR form and the other the other layer(s) in ER forms even with a different releasing time, according to known technologies.

The composition according to the present invention may be in form of a capsule containing two tablets, one of them comprising the active ingredient of formula (I) above in IR form and the other comprising the same active ingredient in an ER form.

The composition may also be formulated in tablets in which one or both of the two components is in controlled-release formulation, for example as a dispersion of said component in hydroxypropyl methyl cellulose or in a film-coated microgranule. Advantageously, the ER-formulation is in the core and the IR-formulation is in the outer layer in multi-layer tablets in which, for example, both the core and the outer layer are coated with a film. Also a three-layer tablet in which each layer releases the active ingredient of formula (I) at different times may also usefully used.

Capsules made of two separated parts, one containing the IR-formulation, and the other the ER-formulation, may be used.

The unit form of the present invention may be a pre-measured volume of a liquid solution or suspension for oral administration, a patch for transdermal application or an aqueous solution for injection or for topical application.

Carriers for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubrifiants such as polyethylenglycol or magnesium stearate; ligands such as methylcellulose, sodium carboxymethylcellulose, alginic acid, alginates; sweeteners, such as sucrose, dextrose, mannitol, saccharin; or flavoring agents such as natural or synthetic oils.

Carriers for orally disintegrating tablets include for example lubricants, aggregating, sweetening, flavoring or disaggregating agents as well as agents improving the buccal mucosa absorption of components (a) and (b) such as sorbitol, mannitol, lactose and cellulose.

Carriers for liquid, normally aqueous, suspensions or solutions include for example antioxidants, such as sodium metabisulfite or sodium sulfite, thickening agents, such as microcrystalline cellulose, hydroxypropylcellulose, carboxymethylcellulose or polyvinylpyrrolidone, preservatives such as methyl paraben, ethyl paraben, sodium ethylenediaminotetracetate, sodium benzoate or an alkaline salt of sorbic acid, as well as flavoring and sweetening agents.

Carriers and vehicles for ER tablets include retardant materials such as is acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof.

The sweeteners contained in the orally disintegrating tablets and the liquid suspensions or solutions may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

The pharmaceutical composition of the present invention is destined to be administered to a human being by oral or parenteral route, for example by injection, by transdermal application, by aerosol or rectally by suppositories. The therapeutic daily dose may vary according to the type and the gravity of the disease, among the aforementioned ones, to be cured, as well as according to the age, the sex and the general condition of the patient to be treated and will be in the range of from 5 to 500 mg, optionally subdivided in two doses.

The following examples illustrate the invention.

Example 1

Propiverine hydrochloride (50 mg, 0.12 mM) is suspended in water (10 ml). 2 M aqueous sodium carbonate (0.5 ml, 1.0 mM) is added and the reaction mixture is extracted twice with ethyl acetate. The organic phase is dried over anhydrous sodium sulfate and concentrated under reduce pressure. The residue is dissolved in dry ethanol (5 ml) and the ethanolic solution is cooled to 0° C. Methyl iodide (25 ml, 0.40 mM) is then added and the reaction mixture is stirred at room temperature for 18 hours (formation of a white solid). The solid formed is filtered off, washed with small amounts of ethanol and dried under vacuum to afford 1,1-dimethyl-4-[(2,2-diphenyl-2-propoxy)acetoxy]piperidinium iodide (methylpropiverinium iodide) as a white solid (30 mg; yield: 48%). Melting point: 248° C.-250° C.

$[C_{24}H_{32}NO_3]^+$ 382.4 (m/z). $^1$H NMR 300 MHz (DMSO $D_6$), d: 0.84 (t, 3H, j=7.5 Hz), 1.50 (qui, 2H, j1=7.5 Hz, j2=6.6 Hz), 1.82 (br.s., 2H), 2.06 (br.s., 2H), 2.91 (br.t., 2H, j=9.3 Hz), 2.94 (s, 3H), 3.02 (s, 3H), 3.14 (t, 2H, j=6.6 Hz), 3.35 (br.s., 2H), 5.00 (m, 1H), 7.37 (m, 10H).

By operating as described above, by using 0.40 mM of methyl bromide instead of the same amount of methyl iodide, 1,1-dimethyl-4-[(2,2-diphenyl-2-propoxy)acetoxy] piperidinium bromide (methylpropiverinium bromide) is obtained.

Example 2

Capsules for oral administration are prepared by mixing the following ingredients:

| Ingredients | Parts by weight |
| --- | --- |
| Methylpropiverinium iodide | 1,500 |
| Mannitol | 4,475 |
| Colloidal silicon dioxide (Aerosil ®) | 25 |

After mixing, the mixture is screened through a 40 mesh screen and introduced in two-piece hard gelatin capsule No. 3 containing 15 mg of methylpropiverinium iodide.

Similarly, capsules containing 20 mg of methylpropiverinium iodide are prepared.

Example 3

Immediate release tablets for oral administration are prepared by mixing 3.5 kg of methylpropiverinium iodide, 0.25 kg of gelatin, 0.25 kg of magnesium stearate and 10 kg of corn starch and forming the mixture into tablets containing 35 mg of methylpropiverinium iodide by a conventional tableting machine.

The invention claimed is:

1. A pharmaceutical composition comprising an effective amount of an 1-alkyl-1-methyl-4-[(2,2-diphenyl-2-propoxy)acetoxy]piperidinium halide of formula

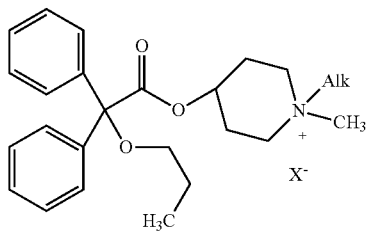

(I)

wherein X is a halogen atom selected from the group consisting of chlorine, bromine and iodine and Alk is a ($C_1$-$C_4$)alkyl group, in admixture with a pharmaceutical carrier.

2. A pharmaceutical composition comprising an effective amount of an 1-alkyl-1-methyl-4-[(2,2-diphenyl-2-propoxy)acetoxy]piperidinium halide of formula

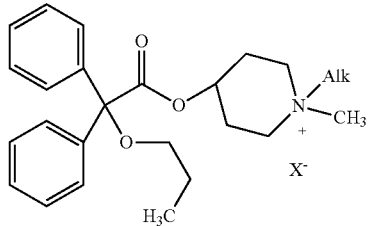

(I)

wherein X is a halogen atom selected from the group consisting of chlorine and iodine, and Alk is a ($C_1$-$C_4$)alkyl group, in admixture with a pharmaceutical carrier.

3. The pharmaceutical composition of claim 1 or 2, wherein Alk is a methyl group.

4. The pharmaceutical composition of claim 1 or 2, wherein said effective amount is from 5 mg to 250 mg.

5. The pharmaceutical composition of claim 1 or 2, wherein said 1-alkyl-1-methyl-4-[(2,2-diphenyl-2-propoxy)acetyl]piperidinium halide of formula (I) is 1,1-dimethyl-4-[(2,2-diphenyl-2-propoxy)acetoxy]piperidinium iodide.

6. The composition of claim 5, wherein the 1,1-dimethyl-4-[(2,2-diphenyl-2-propoxy)acetoxy]piperidinium iodide is present in a tablet at an amount of 35 mg.

7. The composition of claim 1 or 2, wherein the composition is a capsule containing 15 mg of methylpropiverinium iodide.

8. The composition of claim 1 or 2, wherein the composition is a capsule containing 20 mg of methylpropiverinium iodide.

9. The composition of claim 1 or 2, wherein the composition is a capsule containing 35 mg of methylpropiverinium iodide.

* * * * *